United States Patent [19]
Gorcester

[11] Patent Number: 5,519,152
[45] Date of Patent: May 21, 1996

[54] MANUFACTURING ETHYLENE OXIDE

[75] Inventor: Jeffrey P. Gorcester, Amsterdam, Netherlands

[73] Assignee: Shell Oil Company, Houston, Tex.

[21] Appl. No.: 417,481

[22] Filed: Apr. 5, 1995

Related U.S. Application Data

[63] Continuation of Ser. No. 305,122, Sep. 13, 1994, abandoned.

[30] Foreign Application Priority Data

Sep. 20, 1993 [EP] European Pat. Off. .............. 93202726

[51] Int. Cl.⁶ ...................... C07D 301/32; C07D 303/04
[52] U.S. Cl. ........................... 549/541; 549/534; 549/538
[58] Field of Search ................................... 549/538, 534, 549/541

[56] References Cited

U.S. PATENT DOCUMENTS

| | | | |
|---|---|---|---|
| 4,879,396 | 11/1989 | Ozero | 549/534 |
| 4,904,807 | 2/1990 | Ozero . | |
| 5,233,060 | 8/1993 | Pendergast et al. | 549/538 |

FOREIGN PATENT DOCUMENTS

| | | |
|---|---|---|
| 0142005A1 | 5/1985 | European Pat. Off. . |
| 0200518A2 | 11/1986 | European Pat. Off. . |
| 0266271A1 | 5/1988 | European Pat. Off. . |
| 0481363A1 | 4/1992 | European Pat. Off. . |
| 3337572A | 4/1985 | Germany . |

*Primary Examiner*—Joseph E. Evans

[57] ABSTRACT

A process of manufacturing ethylene oxide is presented in ethylene and free oxygen are reacted in the presence of methane, carbon dioxide, and argon in a reactor to form an effluent comprising ethylene oxide; the effluent is then withdrawn and ethylene oxide is removed from the effluent to obtain a recycle stream; carbon dioxide and argon are removed from the recycle stream to obtain a treated recycle stream which is supplied to the reactor along with additional reactants and methane, wherein removing argon comprises separating a side stream from the recycle stream, passing the side stream to the feed inlet of a membrane unit, removing an argon-containing stream from the permeate outlet of the membrane unit, removing a retentate stream from the retentate outlet of the membrane unit, adding the retentate stream to the recycle stream, and purging the permeate side of the membrane unit with inert gas.

11 Claims, 1 Drawing Sheet

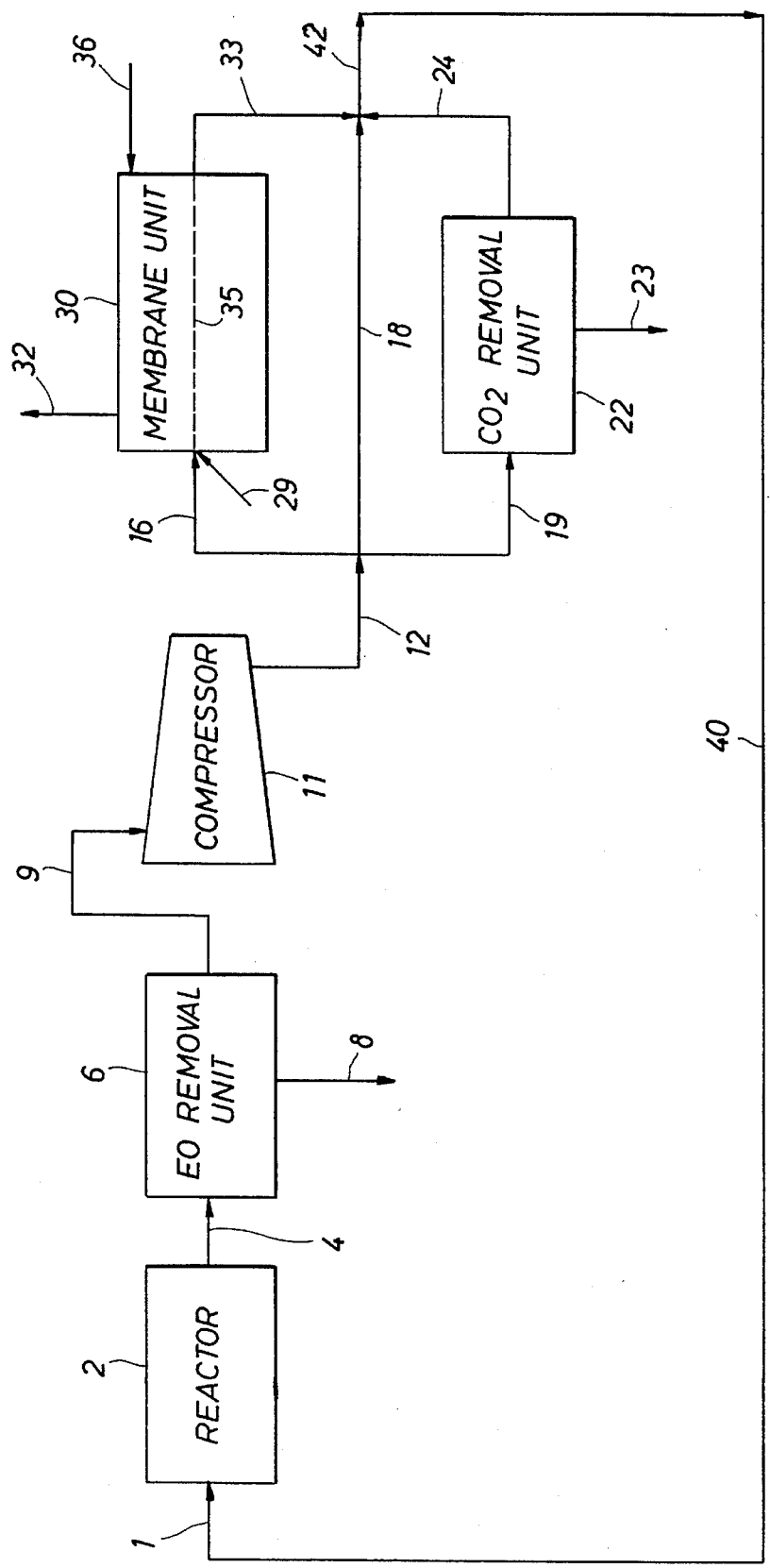

MANUFACTURING ETHYLENE OXIDE

This is a continuation of application Ser. No. 08/305,122, filed Sep. 13, 1994, now abandoned.

FIELD OF THE INVENTION

The present invention relates to the production of ethylene oxide.

BACKGROUND OF THE INVENTION

U.S. Pat. No. 4,904,807 ('807) discloses a process of manufacturing ethylene oxide comprising reacting ethylene and free oxygen in a reactor in the presence of methane to form ethylene oxide (in an effluent containing carbon dioxide and argon); withdrawing the effluent from the reactor; removing ethylene oxide from the reactor effluent to obtain a recycle stream; removing carbon dioxide and argon from the recycle stream to obtain a treated recycle stream; supplying the treated recycle stream to the reactor; and supplying additional reactants and methane to the reactor.

Additional reactants, ethylene and free oxygen-containing gas, are supplied to the reactor to replace the reactants which reacted to ethylene oxide. Methane is supplied to maintain the methane concentration at such a level that its presence is beneficial to the efficiency of the reaction as described in U.S. Pat. No. 3,119,837.

Carbon dioxide is a by-product of the reaction and part of the carbon dioxide is removed to maintain the concentration of carbon dioxide below a predetermined level.

Argon enters into the process with the free oxygen-containing gas. In order to maintain the argon concentration below a predetermined level, a portion is removed from the recycle stream downstream of the removal of ethylene oxide. In addition trace amounts of nitrogen enter into the process with the free oxygen-containing gas.

In the process of the '807 patent, removing argon comprises separating a side stream from the recycle stream, passing the side stream to the feed inlet of a membrane unit, removing an argon-containing stream from the permeate outlet of the membrane unit, removing a retentate stream from the retentate outlet of the membrane unit, and adding the retentate stream to the recycle stream.

As the flow through the membrane is large, the area of the membrane is large as well. The area of the membrane could be reduced and the overall ethylene oxide process could be made more efficient by increasing the rate of the extraction of argon through the membrane used to extract it. Furthermore, given the combination of combustible reactants, intermediates, and products in ordinary reaction conditions, additional process measures which make the process safer yet would be beneficial.

SUMMARY OF THE INVENTION

It is an object of this invention to improve the efficiency of the process of making ethylene oxide from ethylene and oxygen.

It is a further object of the invention to improve the efficiency of the removal and recycle of useful substances from a reaction effluent in the process for making ethylene oxide.

It is a yet further object of the present invention to reduce the area of a membrane/membrane unit used to extract inert matter from an effluent in the process for making ethylene oxide.

These and other objects are accomplished by providing a process of manufacturing ethylene oxide comprising: reacting ethylene with free oxygen in a reactor to obtain an effluent stream comprising ethylene oxide, passing the effluent stream through a membrane permeable to argon so that argon is separated therefrom; and purging the membrane with a countercurrent of a gas inert to the effluent stream.

In one aspect of the invention, the process comprises: reacting ethylene and free oxygen in the presence of methane in a reactor to form an effluent comprising ethylene oxide carbon dioxide and argon; withdrawing the effluent; removing ethylene oxide from the effluent to obtain a recycle stream; removing carbon dioxide and argon from the recycle stream to obtain a treated recycle stream; supplying the treated recycle stream to the reactor; and supplying additional reactants and methane to the reactor, wherein removing argon comprises separating a side stream from the recycle stream, passing the side stream to the feed inlet of a membrane unit, removing an argon-containing stream from the permeate outlet of the membrane unit, removing a retentate stream from the retentate outlet of the membrane unit, adding the retentate stream to the recycle stream, and purging the permeate side of the membrane unit with inert gas.

DETAILED DESCRIPTION

DESCRIPTION OF THE DRAWING

Turning to the Figure, a mixture including ethylene, free oxygen-containing gas and methane is supplied through conduit, 1 to a reactor, 2. In the reactor, 2 ethylene and free oxygen are allowed to react to ethylene oxide in the presence of methane and contaminants such as carbon dioxide and argon. The reactor, 2 contains a suitable catalyst. U.S. Pat. No. 4,833,261 provides an example of catalysts and reaction conditions that can be used in the process for making ethylene oxide by the reaction of ethylene and free oxygen and is incorporated by reference.

From the reactor, 2 a reactor effluent is withdrawn through conduit, 4. The reactor effluent includes ethylene oxide, carbon dioxide, methane and argon. Carbon dioxide is a by-product of the reaction, a further by-product is ethane. Argon and trace amounts of nitrogen are introduced into the process along with the free oxygen-containing gas.

Ethylene oxide is removed from the effluent in an ethylene oxide removal unit, 6. This done in two streams. An ethylene oxide-containing stream is removed through conduit, 8 and a recycle stream through conduit, 9.

The other contaminants are removed downstream of the ethylene oxide removal unit. The recycle stream is compressed in compressor, 11 to compensate for the pressure drops in the treating units. The compressed recycle stream then runs through conduit, 12 and is divided into a side stream, 16 and a main stream. The main stream is divided into two streams, 18 and 19. Carbon dioxide is removed from stream, 19 in carbon dioxide removal unit 22. The carbon dioxide containing stream is removed from the carbon dioxide removal unit, 22 through conduit, 23. A treated stream having a reduced carbon dioxide content is removed through conduit, 24. The flow rate of the side stream, 16 is between 1 and 5% of the flow rate of the recycle stream, the flow rate of stream, 19 is between 10 and 40% of the flow rate of the recycle stream, and the flow rate of stream, 18 is the balance. In an alternative embodiment, carbon dioxide can be removed from the main stream, so that dividing the main stream can be omitted.

Removing argon from the recycle stream comprises passing the side stream, 16 to the feed inlet, 29 of a membrane unit 30, removing an argon-containing stream from the permeate outlet 32, and removing a treated stream from the retentate outlet 33. The membrane unit, 30 comprises a hollow fiber membrane schematically represented by line 35. The membrane material can be any material that allows selective permeation of argon. Preferably, the membrane is comprised of hollow fibers of a dense polymeric material. Polysulfone and polydimethyl siloxane are most preferred membrane materials.

To purge the retentate side of the membrane unit, 30, inert gas is supplied to the membrane unit, 30 through conduit, 36. Preferred inert gases are methane, nitrogen, carbon dioxide, or mixtures of these gases. The inert gas flows counter-currently through the retentate side of the membrane unit, 30. The flow rate of the purge gas is in the range of from 1 to 10 mol % of the feed flow rate; the amount of ethylene permeating through the membrane decreasing with increasing purge gas flow rate. Membrane units having 25% less membrane area than prior art units can achieve increases of 6% v of ethylene recovery. Moreover, the countercurrents of inert gases better control oxygen concentration in reject streams thereby lowering the threat of creating an explosive mixture.

The treated stream, 24 from the carbon dioxide removal unit, 22 and the treated stream, 33 from the membrane unit, 30 are combined with the untreated stream, 18 and supplied through conduit, 40 and conduit, 1 into the reactor, 2. Additional reactants, ethylene and free oxygen-containing gas, and methane are supplied to the reactor, 2 through conduit, 42 which opens into conduit, 40.

EXAMPLES

Example 1 (Comparative Hypothetical)

In this example, the process disclosed in U.S. Pat. No. 4,879,396 is used to produce ethylene oxide. A computer simulation was used to generate Table 1 which provides flow rates of the components in the feed to a membrane unit, the retentate, and the permeate leaving the membrane unit. No purge gas is used in this example. The membrane unit includes a hollow fiber comprised of polysulfone. The membrane has an area of 1,630 m$^2$.

TABLE 1

|  | Feed | | Permeate | | Retentate | |
| --- | --- | --- | --- | --- | --- | --- |
|  | % vol | kmol/h | % vol | kmol/h | % vol | kmol/h |
| Nitrogen | 1.22 | 4.54 | 0.81 | 0.14 | 1.24 | 4.40 |
| Argon | 9.30 | 34.60 | 11.88 | 2.09 | 9.17 | 32.51 |
| Oxygen | 4.16 | 15.48 | 7.70 | 1.36 | 3.98 | 14.12 |
| Methane | 50.24 | 186.90 | 38.36 | 6.75 | 50.83 | 180.15 |
| Ethylene | 27.20 | 101.19 | 22.72 | 4.00 | 27.42 | 97.19 |
| Ethane | 0.95 | 3.53 | 0.63 | 0.11 | 0.97 | 3.42 |
| Carbon dioxide | 6.93 | 25.78 | 17.90 | 3.15 | 6.39 | 22.63 |
| Total | 100.00 | 372.02 | 100.00 | 17.60 | 100.00 | 354.42 |

Example 2 (Hypothetical According to the Invention)

In this example, the process according to the instant invention is used to produce ethylene oxide. Methane is used to purge the membrane unit at its retentate side so as to be introduced in countercurrent fashion. The flow rate of the purge gas is 7.44 kmol methane per hour, which corresponds to 2 mol % of the feed flow rate. No purge gas is used.

A computer simulation was used to generate Table 2 which gives the compositions and the flow rates of the components in the feed to a membrane unit, in the retentate, and the permeate leaving the membrane unit. The membrane unit includes a hollow fiber membrane comprised of polysulfone having an area of 1,310 m$^2$.

TABLE 2

|  | Feed | | Permeate | | Retentate | |
| --- | --- | --- | --- | --- | --- | --- |
|  | % vol | kmol/h | % vol | kmol/h | % vol | kmol/h |
| Nitrogen | 1.34 | 4.99 | 0.59 | 0.14 | 1.36 | 4.85 |
| Argon | 9.28 | 34.52 | 8.85 | 2.09 | 9.11 | 32.44 |
| Oxygen | 4.15 | 15.44 | 7.19 | 1.70 | 3.86 | 13.74 |
| Methane | 50.12 | 186.46 | 50.09 | 11.82 | 51.17 | 174.64 |
| Ethylene | 27.14 | 100.97 | 15.54 | 3.67 | 27.35 | 97.30 |
| Ethane | 1.06 | 3.94 | 0.47 | 0.11 | 1.08 | 3.83 |
| Carbon dioxide | 6.91 | 25.71 | 17.28 | 4.08 | 6.07 | 21.63 |
| Total | 100.00 | 372.02 | 100.01 | 23.60 | 100.00 | 348.42 |

Comparing the performances of the two membrane units, it is clear that when the process for making ethylene oxide is conducted according to the present invention, the same amount of argon passes through a membrane with a significantly smaller area, and a smaller amount of ethylene passes through the membrane compared to methods of the prior art.

The foregoing examples are submitted only for the purposes of illustration and are not presented by way of limitation.

What is claimed is:

1. An improved process for removing argon from an effluent stream comprising ethylene oxide produced by the reaction of ethylene and oxygen, said improved process comprising:

passing said effluent stream through a membrane permeable to argon so that argon is separated therefrom; and purging said membrane with a countercurrent of a gas inert to said effluent stream.

2. The process of claim 1 wherein said membrane is comprised of hollow polymeric fibers.

3. The process of claim 1 wherein said fibers are selected from the group consisting of polysulfone and polydimethyl siloxane.

4. The process of claim 1 wherein said gas inert to said effluent stream is selected from the group consisting of methane, nitrogen, carbon dioxide, and mixtures thereof.

5. The process of claim 1 wherein the flow rate of said gas inert to said effluent stream comprises between about 1 and 10 mol % of the flow rate of said effluent stream into said membrane.

6. In a process for producing ethylene oxide by reacting ethylene and oxygen wherein argon is then removed from an effluent stream comprising ethylene oxide and said effluent stream is passed through a membrane to separate various gases from the effluent stream the improvement which comprises:

purging said membrane with a countercurrent of a gas inert to said effluent stream.

7. The process of claim 6 wherein said membrane is housed in a membrane unit having a permeate side terminating in a permeate outlet and a retentate side terminating in a retentate outlet; wherein a stream comprising argon is removed from said permeate outlet and a stream substantially free of argon is removed from said retentate outlet.

8. The process of claim 7 wherein said gas inert to said effluent stream is supplied to said retentate side.

9. A process of manufacturing ethylene oxide comprising: reacting ethylene and free oxygen in a reactor in the presence of methane to form a reactor effluent comprising ethylene oxide, carbon monoxide, and argon; withdrawing the reactor effluent from the reactor; removing ethylene oxide from the reactor effluent to obtain a recycle stream; removing carbon dioxide and argon from the recycle stream to obtain a treated recycle stream; supplying the treated recycle stream to the reactor; and supplying additional reactants and methane to the reactor, wherein removing argon comprises separating a side stream from the recycle stream, passing the side stream to the feed inlet of a membrane unit, removing an argon-containing stream from the permeate outlet of the membrane unit, removing a retentate stream from the retentate outlet of the membrane unit, adding the retentate stream to the recycle stream, and purging the permeate side of the membrane unit with inert gas.

10. The process as claimed in claim 9, wherein said inert gas is passed counter-currently along the membrane.

11. The process of claim 9, wherein the flow rate of said inert gas is from 1 to 10 mol % of the flow rate of said side stream into said feed inlet of said membrane unit.

* * * * *